United States Patent [19]

Dohzono et al.

[11] Patent Number: 4,714,466
[45] Date of Patent: Dec. 22, 1987

[54] ABSORBENT MEMBER FOR TAMPON

[75] Inventors: Masatake Dohzono; Iwao Miyashita; Norihiro Abe, all of Utsunomiya, Japan

[73] Assignee: Kao Corporation, Tokyo, Japan

[21] Appl. No.: 816,860

[22] Filed: Jan. 7, 1986

[30] Foreign Application Priority Data

Jan. 25, 1985 [JP] Japan .................................. 60-12244
Jan. 25, 1985 [JP] Japan .................................. 60-12247

[51] Int. Cl.⁴ ............................................. A61F 13/16
[52] U.S. Cl. ........................................ 604/378; 604/904
[58] Field of Search ................. 604/378, 379, 385.1, 604/367, 374, 375, 11, 904

[56] References Cited

U.S. PATENT DOCUMENTS

| | | | |
|---|---|---|---|
| 3,340,874 | 9/1967 | Burgeni | 604/379 |
| 3,424,163 | 1/1969 | Gravdahl | 604/379 X |
| 4,449,979 | 5/1984 | Holtman | 604/379 |
| 4,496,358 | 1/1985 | Karami et al. | 604/379 |
| 4,551,142 | 11/1985 | Kopolow | 604/379 |
| 4,578,070 | 3/1986 | Holtman | 604/379 |

Primary Examiner—John D. Yasko
Attorney, Agent, or Firm—Birch, Stewart, Kolasch & Birch

[57] ABSTRACT

An absorbent member, suitable for a tampon, is produced by ejecting a liquid against a sheet of water-absorptive fibers in order to interlace the fibers with each other and moulding under a pressure the sheet to form the absorbent member.

8 Claims, 13 Drawing Figures

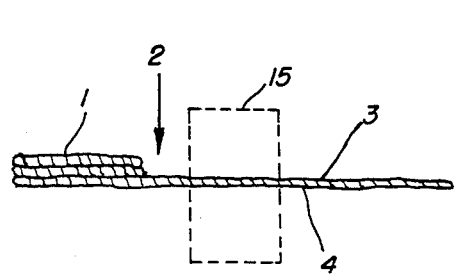
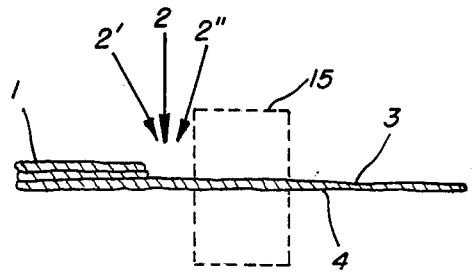
FIG. 1  FIG. 2
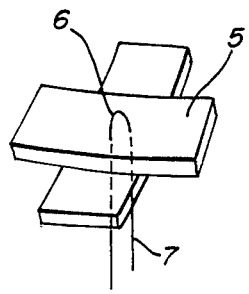
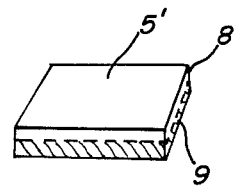
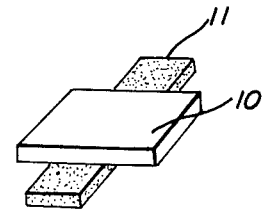
FIG. 3  FIG. 4  FIG. 5
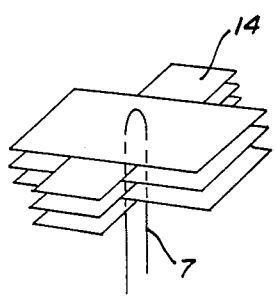
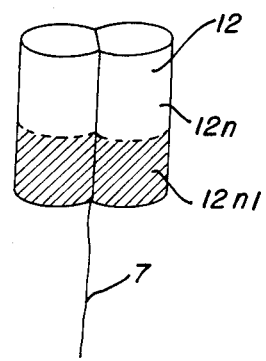
FIG. 6  FIG. 7
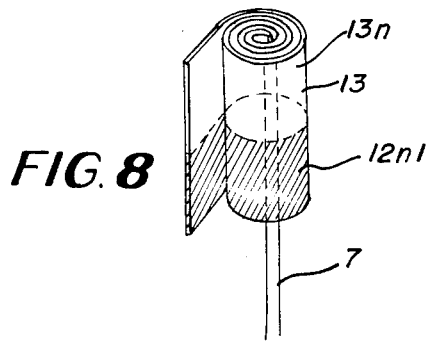
FIG. 8

ABSORBENT MEMBER FOR TAMPON

The invention relates to an absorbent member for a tampon and a sanitary article for women needing the same. It further concerns a process for production of the absorbent member.

STATEMENT OF PRIOR ARTS

It is known that a tampon is produced, for instance, by cutting a laminated sheet of water-absorptive fibers into rectangle pieces, attaching a pulling-out string to each piece and moulding the piece under a pressure to a tampon. In another production, a web sheet of water-absorptive fibers is wound to form a volute cylinder and moulded under a pressure to a tampon. After use of such a conventional tampon, however, some fibers disadvantageously happen to fall off by contact and frictional resistance of the swollen tampon due to absorption of menstrual blood on the vaginal wall.

With a view to reducing the amount of a fiber falling off, a method of integration of a fiber laminated by needling is disclosed in Japanese Patent Laid-Open No. 59498/1974. According to this method, mutual interlacing of the fiber is improved. However, the fiber is so damaged because of needling with a metallic needle as to locally form short fibers. Thus the effect of reducing the amount of the falling fiber is not sufficient. Besides, a needle is sometimes broken and incorporated into a tampon in the molding thereof. Thus such a tampon is very dangerous as a sanitary disposal article to be used by inserting the same into a vagina. Thus this method in regrettably inadequate as the method of integration of the fiber laminate.

A proposal as to attachment of a pull-out string has been made in Japanese Utility Model Publication No. 25,376/1984. However, the method is unsatisfactory particularly from the viewpoint of falling off of minute fibers (fiber dust) and a short fiber.

Further, Japanese Utility Model Publication No. 25,377/1984 discloses a device aimed at achieving the same purpose as that of this invention. However, since a hydrophobic fiber is disposed around the peripheral surface of a tampon, there arises a defect that the rate of absorption is lowered for a high viscosity liquid such as menstrual blood.

A slow rate of absorption of a high viscosity liquid such as menstrual blood as mentioned above is a common problematic defect among conventional tampons. This generally ensues from the menstrual blood absorption-inhibiting properties of a lubricant (finishing agent) and impurities in the step of fiber manufacturing which stick to the water-absorptive fibers constituting the absorbent member of a tampon. The absorbent member of a tampon generally comprises a water-absorptive fiber, such as rayon, as the constituent material. However, a lubricant is applied to such a fiber allowing the steps of spinning, knitting, dyeing, etc. to be easily practiced. More specifically, the lubricant is employed for satisfying the requirements such as flexibility, smoothness, adequate frictional properties, and antistatic properties. In spite of the above, it has been found that the rate of absorption is, in general, increased when a tampon is formed by using a fiber laminate containing decreased amounts of a lubricant and impurities by water washing thereof or the like. Accordingly, it can be concluded that the absorption rates of conventional tampons are slowed by a lubricant, etc. sticking to a fiber, which is necessary for manufacturing and processing of a fiber laminate.

In general, this kind of tampon, which is formed by compression-molding a water absorptive fiber into a cylindrical shape, gradually absorbs menstrual blood from the tip portion thereof to be gradually swollen from the tip portion when it is inserted into a vagina. However, since the tampon is compression-molded with a amount of the fiber large enough to have a high fiber density for providing a sufficient capacity of absorption of menstrual blood and facilitating insertion thereof into a vagina, the rate of absorption of menstrual blood is slow with a difficulty in swelling, so that menstrual blood may sometimes leak along the side of the tampon.

An invention aiming at obviating such defects is disclosed in Japanese Patent Publication No. 17,583/1980. A known method disclosed therein is characterized in that it provides a density of 0.2 to 0.8 $g/cm^3$ in the tip portion of the absorbent member of a tampon, a density of 0.8 to 1.5 $g/cm^3$ in the rear portion of the member, and a length of the tip portion of 1/10 to ½ the total length of the absorbent member of a tampon. However, although a tampon produced according to this known method surely has a high rate of absorption and a high capacity of absorption for a low-viscosity liquid such as water, the tampon does not have a sufficiently high rate of absorption for a high-viscosity liquid such as menstrual blood. Thus, the method can not obviate the defects of the conventional absorbent member of a tampon as mentioned above. This is because a lubricant (finishing agent) such as rayon is generally applied to a water-absorptive fiber, and employed in the absorbent member of a tampon, leading to occasional obstruction of absorption of menstrual blood, and because the fiber density of 0.8 to 1.5 $g/cm^3$ in the rear portion is too high, leading to a difficulty in absorption of menstrual blood. The purpose of application of a lubricant to a fiber is to satisfy various purposes such as spinning, knitting, dyeing, and antistatic treatment. Thus application of the lubricant is indispensable from the viewpoint of processability.

The conventional absorbent member of a tampon is generally produced according to, for example, a method comprising compression-molding a loose fiber piece, such as a fiber web, having a basis weight of about 300 to 1,000 $g/m^2$ in the diametrical and lengthwise directions thereof either as it is or after it is folded, or a method comprising compressing the fiber web, having a basis weight of about 40 $g/m^2$, in the diametrical direction thereof after it is rolled into a volute form. However, since the fiber web generally contains minute fibers (fiber dust) and short fibers of 10 mm or less in length and has a low degree of mutual fiber interlacing, there is a defect that the fiber falls off and remains in the vagina when the tampon is pulled out after service thereof. More specifically, part of the fiber constituting the absorbent member of the tampon, particularly part of the fiber constituting the peripheral surface of the tampon, defectively falls off and remains in the vagina by contact of the swollen tampon due to menstrual blood and/or when inserted into the vagina the vaginal wall provides frictional resistance when pulling out the tampon.

As described above, conventional sanitary tampons have the following defects.

(1) The amount of a fiber falling off when pulling out a tampon after service is large.

(2) The rate of absorption of a high-viscosity liquid such as menstrual blood is small.

SUMMARY OF THE INVENTION

According to the invention, an absorbent member, suitable for a tampon, is produced by the steps of ejecting a liquid against a sheet of water-absorptive fibers in order to interlace the fibers with each other and moulding, under a pressure, the sheet to form the absorbent member. The ejection step makes the water-absorptive fibers, having been formed into a sheet, interlace with each other, coil around each other, get twisted, cling to each other or entwine. The invention provides an absorbent member which has been produced by the above defined process. A preferable embodiment of the absorbent member according to the invention comprises a first portion on the front part and a second portion on the rear part, said first portion having a smaller fiber density than the second portion.

Specifically, in accordance with the present invention, there is provided an absorbent member of a tampon characterized in that it is formed by ejecting a liquid against a fiber laminate mainly comprising a water-absorptive fiber to interlace the fiber and compression-molding the resulting sheet-like material.

BRIEF DESCRIPTION OF THE DRAWING

FIGS. 1 and 2 are rough crossectional illustrations of processes of preparation of the fiber sheet-like material to be employed in the absorbent member of a tampon according to the present invention.

FIGS. 3, 5 and 6 are perspective views showing the state of compression-molding fiber sheet-like materials.

FIG. 4 is a perspective view of an example of a fiber sheet-like material in accordance with the present invention.

FIGS. 7 and 8 are perspective views showing examples for other shapes of tampons.

FIG. 9 shows a preferable example of a sheet of fibers to use in the invention.

FIG. 10 shows an example of the invention tampon in the front view.

FIG. 11 shows another example of a sheet of fibers to use in the invention.

FIG. 12 also indicates an example of a sheet of fibers to use in the invention.

Figure 9:
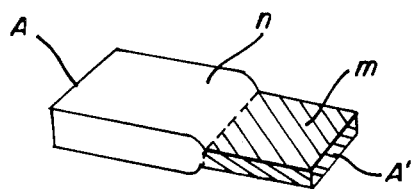
FIGS. 9 to 12 illustrates a preferable embodiment of the invention absorbent member which comprises the first and the second portions.

1: fiber laminate
2, 2', 2'': arrow showing the direction of ejection of ejection of a liquid
3: fiber sheet-like material
4: belt
5, 5': rectangular fiber sheet
6: central portion
7: string
8: portion having a low degree of interlacing
9: portion having a high degree of interlacing
10: fiber sheet-like material having a low degree of interlacing
11: fiber sheet-like material having a high degree of interlacing
12: water-absorptive fiber laminate
13: water-absorptive fiber web
14: fiber sheet having a relatively light basis weight
15: drying apparatus
16: laminate of sheets of fibers
17: sheet of fibers
m: the second part of the absorbent member
n: the first part of the absorbent member.

In this invention, a fiber web mainly comprising a water-absorptive fiber is formed by a spinning card, a garnett or other apparatus. A fiber laminate is obtained by laminating the fiber web either as such or by using an adequate method. Methods of lamination of a fiber include one wherein fibers are arranged substantially in parallel in the lengthwise direction of the web (parallel-laid lamination) and one wherein fibers are arranged by folding the web (cross-laid lamination). A fiber laminate 1 as shown in FIG. 1 is formed by one of these methods. The fiber laminate may be obtained according to a method of non-directional random arrangement (air-lay) of a fiber.

The fiber laminate 1 thus obtained is transferred on a belt 4 to a liquid ejection step. In the liquid ejection step, a liquid is ejected against the fiber laminate 1 in a direction of an arrow 2 as shown in FIG. 1. The liquid is generally water. However, heated water such as warm water or hot water may sometimes be effective for the purpose of washing out a lubricant and other impurities sticking to the fiber is accordance with the present invention. After ejection of the liquid in this way, the fiber laminate was dried in a drying apparatus 15 to form a fiber sheet-like material 3 in which the fiber is interlaced. In the present invention, the degree of interlacing of the fiber constituting the fiber laminate is significant, and washing out the lubricant sticking to the fiber is important. The key point of attaining the above is the ejection pressure of the liquid. More specifically, the ejection pressure is preferably 10 kg/cm$^2$ or higher. A fiber sheet prepared at a pressure below the above value is so low in the degree of fiber interlacing that the amount of the fiber falling off in compression-molding of a tampon may be large, and that the effect of washing out the lubricant cannot be expected so much. Besides, the effect of removing a minute and/or short fiber contained in the fiber laminate is unsatisfactory. Here, the short fiber generally refers to a fiber of 10 mm or less in length. The kind of water-absorptive fiber constituting the fiber laminate may be any one of those generally used in tampons, such as rayon, dewaxed cotton, or a mixture thereof. A small amount of a hydrophobic fiber may be blended therewith. The fiber size is not particularly limited. However, a size of about 1 to 5 deniers is adequate from the viewpoint of water absorption performance as the fiber used in tampons. A fiber length of 20 mm or more, especially 30 mm or more, is adequate for the purpose of reducing the amount of the fiber to fall off in accordance with the present invention.

The basis weight of the fiber laminate 1 against which the liquid is ejected depends on the shape of tampons obtained by compression molding but is not particularly limited.

In the above-mentioned method of interlacing a fiber by ejecting a liquid there against, the degree of fiber interlacing may sometimes be affected by the shape, etc. of a nozzle used for liquid ejection. However, in preparation of a water-absorptive fiber sheet-like material according to the present invention, any shape of a nozzle may be employed. Besides, a method of ejecting a liquid simultaneously in different directions 2, 2', and 2'' as shown in FIG. 2, and a method of simultaneously or separately ejecting a liquid against the fiber laminate 1 from both the upper and lower sides thereof can be mentioned as the method of efficiently conducting fiber interlacing.

Further alternatively, a fiber sheet-like material to be compression-molded into the absorbent member of a tampon according to the present invention may be obtained according to a method of ejecting a liquid against a fiber laminate superimposed on a non-woven fabric mainly comprising a water-absorptive fiber as a base cloth or a fiber laminate sandwiched between such base cloths in the same manner of ejection as shown in FIG. 1 or 2. The sheet thus obtained has a merit that it has an increased strength enough to make handling thereof easy since it comprises the non-woven fabric.

As an example of the method of compression-molding the fiber sheet-like material in accordance with this invention, there can be mentioned a method comprising crosswise laminating two pieces of rectangular absorbent fiber sheets 5 by cutting an absorbent sheet-like material into an adequate size, attaching a string 7 to the laminate in the central portion 6 thereof in such a way as to allow the string to protrude in that portion as the rear end, and compression-molding the assembly, as shown in FIG. 3. The absorbent member of a tampon thus obtained opens like a parachute due to swelling thereof when it absorbs menstrual blood. Thus, menstrual blood hardly leaks. Besides, the tampon is characteristically easily pulled out after service thereof. In compression molding of a tampon according to the method as shown in FIG. 3, there may be employed a fiber sheet 5' as shown in FIG. 4 which is subjected to much repeated ejection of a liquid on one side 9 thereof and to no ejection or a few ejections of a liquid on the other side 8 thereof. In this case, since there is a difference in the degree of fiber interlacing between the obverse side and reverse side of the fiber sheet, compression molding conducted after lamination as shown in FIG. 3 is made in such a way that the side 8 having a low degree of fiber interlacing is disposed on the inner side of the tampon while the side 9 having a high degree of fiber interlacing is disposed on the outer side of the tampon. In this instance, a difference in the frequency of ejection is provided between both the sides of the fiber laminate. The same purpose can be attained by providing a difference in the pressure of ejection between both sides.

In another instance, a fiber sheet 11 having a high degree of interlacing and a fiber sheet 10 having a low degree of interlacing may be prepared and laminated in such a way as to dispose the fiber sheet 10 having the low degree of interlacing on the inner side of a tampon as shown in FIG. 5, followed by compression molding.

In still another instance shown in FIG. 6, a fiber sheet 14 having a relatively light basis weight is prepared, and a large number of pieces of the sheet is alternately superimposed, as shown in FIG. 3, followed by compression molding. In this case, the tampon obtained easily opens when absorbing menstrual blood due to a large repulsive force of the fiber. Alternately, ejection of a liquid for fiber interlacing may be conducted after superimposition of pieces of a fiber laminate as shown in FIG. 3, followed by compression molding.

The feature of the absorbent member of a tampon according to the present invention consists in use of a fiber sheet-like material subjected to ejection of a liquid to effect fiber interlacing. Thus, those having a shape as shown in FIG. 7 or 8 are included in the scope of this invention. Further, the absorbent member of a tampon according to this invention which is mounted on a so-called applicator is included in the scope of this invention, too.

Since the absorbent member of a tampon according to the present invention is high in the degree of fiber interlacing and low in the content of short fiber at least on the outer side of the absorbent member of the tampon in contact with a vaginal wall, falling off of the fiber hardly occurs when pulling out the tampon swollen by absorption of menstrual blood during or after service thereof. Furthermore, since the amount of lubricant sticking to the fiber is small, the rate of absorption of a high-viscosity liquid such as menstrual blood is high. Particularly, the absorbent member of a tampon obtained by laminating the fiber sheet 5' as shown in FIG. 4 in a way as shown in FIG. 3 and compression-molding the same provides an ideal tampon having a large capacity of absorption which hardly allows leakage.

Then, the invention will be illustrated in respect to a preferable embodiment in which the absorbent member has different fiber densities therein.

Before the compression-moulding step, an absorbent member of the invention is shown in FIGS. 7 and 8. The second part, 12m, 13m, for the rear portion of the absorbent member, hatched in the drawing, has a higher fiber density than the other part. In comparison, the first part 12n, 13n for the front portion of the absorbent member, which will first contact with menstrual blood when the tampons are inserted into vaginas, are lower in fiber density. In order to provide a high fiber density and a low fiber density in the fiber laminate to be compression-molded into the absorbent member of the tampon, the ejection pressure of a liquid against the fiber laminate only has to be varied between portions of the fiber laminate. Thus, the portion subjected to ejection at a high pressure can be made high in fiber density, while the portion subjected to ejection at a low pressure can be made low in fiber density. Alternatively, the number liquid ejections against the fiber laminate may be varied between portions of the fiber laminate to provide a high fiber density in the portions subjected to a large number of ejections and a low fiber density in the portion subjected to a small number of ejection.

Figure 10:
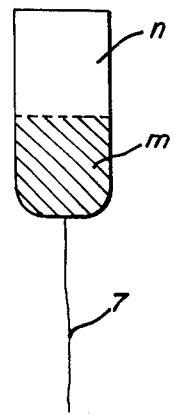

FIG. 9 shows an example of the sheet of fibers in which the fibers have been interlaced with one another according to the above shown step. It is attached to a string as shown in FIG. 7 in the direction of A and A' and then moulded under a pressure to form a tampon as shown in FIG. 10.

According to the method, the portion n having a low fiber density in the sheet gets thicker, while the portion m having a high fiber density gets thin. This is shown in FIG. 9. This is favorable for the tampon, because the tampon can be easily pulled out due to a smaller volume of the rear portion of the tampon than that of the front portion thereof when pulling out the tampon after service thereof since the absorbent member of the tampon, which is a compressed product of fiber, has a tendency of returning, upon absorption of menstrual blood, to the original shape of the fiber sheet-like material before absorption of menstrual blood.

Figure 11A:
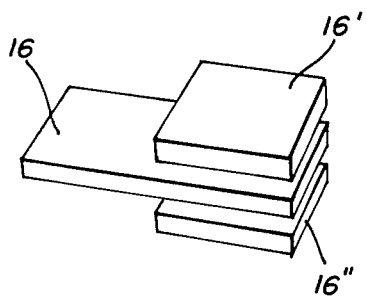
FIG. 11(a) illustrates the state before the ejection and (b), the state after the ejection treatment.
Figure 11B:
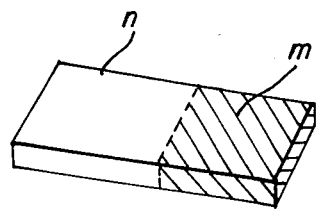

The second method of providing high and low fiber densities is a method comprising superimposing fiber laminates 16, 16' and 16" having adequate basis weights as shown in FIG. 11(a) and ejecting a liquid against the resulting laminate to form a fiber sheet-like material having a substantially uniform thickness as shown in FIG. 11(b). Since the hatched portion m has a high fiber density while the other portion n has a low fiber density according to this method, the absorbent member of the produced tampon has a high rate of absorption in the tip portion thereof.

Figure 12:
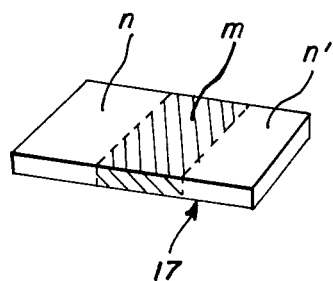

Another Example will now be described. A rectangular sheet of fibers is formed to have a lower fiber density in both outer portions n, n' than in the central portion m. Two sheets such as this are laminated to form a cross. This method is shown in FIG. 12 and then FIG. 13. A string 7 is attached to the laminate in the central portion thereof in such a way as to allow the string to protrude in that portion as the rear end, followed by compression moulding. This way a tampon shown in FIG. 10 is obtained. Such a tampon has an excellent feature that it opens like a parachute due to swelling thereof when it absorbs menstrual blood, as can be understood from the process of production, so that menstrual blood hardly leaks, and that the tampon can be easily pulled out after service thereof.

Here, consideration will be given to the fiber density of the tampon. As described above, the tampon according to this invention is formed by such compression molding as to provide a lower fiber density in the first part n constituting the front portion thereof than the fiber density in the second part constituting the rear portion thereof. Several kinds of absorbent members of tampons as shown in FIG. 7 were tentatively prepared which differ in the densities of the first and second parts thereof and the volume proportion of the first and second parts relative to the whole of absorbent member of the tampon as shown in Table 1. As to these absorbent members of tampons, the rates of absorption were exprimentally examined by using the following three kinds of test liquids.

The testing conditions were as follows.

(1) Method of Ejection of Liquid:
Warm water of 50° C. was ejected through nozzles having a diameter of 0.16 mm at a pressure of 40 to 80 kg/cm². The distance between nozzles was 0.167 mm.

(2) Size of Tampon: 11 mm in diameter, 50 mm in length (3) Fiber Used: rayon of 3 deniers and 51 mm (4) Test Liquids:
[water] aqueous Congo Red solution of 4 cps (25° C.)
[blood A] equine defibrinated blood of 28 cps in viscosity (25° C.)
[blood B] equine defibrinated blood of 83 cps in viscosity (25° C.)

(5) Test Method:
A tampon was set in a elastic rubber tube having an internal diameter of 10 mm. In a state of the tip of the tampon being on the upper side, 5 g of a test liquid was poured on the tip of the tampon at a stroke. The time till completion of absorption of the liquid was measured.

(6) Calculation of Density:
The tampon was separated into two parts at the face where the density sharply changed. The average densities of the first part constituting the front portion and the second part constituting the rear portion, and the overall average density of the absorbent member of the tampon were calculated.

The test results are shown in Table 1.

TABLE 1

| Ejection of liquid | No. | First part Density (g/cm³) | First part Proportion (%) | Second part Density (g/cm³) | Second part Proportion (%) | Average density (g/cm³) | Rate of absorption (sec). Water | Rate of absorption (sec). Blood A | Rate of absorption (sec). Blood B |
|---|---|---|---|---|---|---|---|---|---|
| | | | | Example of this invention | | | | | |
| made | 1 | 0.2 | 50 | 0.6 | 50 | 0.4 | 3 | 9 | 29 |
| | 2 | 0.2 | 40 | 0.7 | 60 | 0.5 | 3 | 10 | 33 |
| | 3 | 0.3 | 50 | 0.5 | 50 | 0.4 | 3 | 12 | 30 |
| | 4 | 0.3 | 50 | 0.7 | 50 | 0.5 | 4 | 14 | 43 |
| | 5 | 0.4 | 60 | 0.65 | 40 | 0.5 | 4 | 16 | 48 |
| | 6 | 0.5 | 40 | 0.8 | 60 | 0.68 | 5 | 26 | 62 |
| | | | | Comparative examples | | | | | |
| not made | 7 | 0.3 | 50 | 0.7 | 50 | 0.5 | 4 | 30 | 85 |
| | 8 | 0.5 | 50 | 0.5 | 50 | 0.5 | 5 | 34 | 122 |
| | 9 | 0.5 | 40 | 0.8 | 60 | 0.68 | 6 | 61 | 865 |
| | 10 | 0.8 | 50 | 0.8 | 50 | 0.8 | 7 | 93 | not absorbed* |

(Note)
*3,600 sec. or more

In Table 1, when the test liquid is water, those not lowered in fiber density in the first part of the absorbent member of the tampon as compared with that in the second part thereof (Nos. 8 and 10) as well as those having considerably high fiber densities in both the first and second parts (Nos. 9 and 10) showed a high rate of absorption and, hence, looked as if they were excellent as the absorbent member of the tampon. However, menstrual blood to be actually absorbed has a high viscosity. Therefore, those having a high rate of absorption of a high-viscosity liquid such as blood A or blood B are desired as the absorbent member of the tampon.

As can be seen in a comparison of No. 4 with No. 7 in Table 1, the absorbent member of the tampon according to the present invention had a high rate of absorption since the amount of a lubricant sticking to the fiber was decreased by ejection of a liquid. Besides, the lowered density in the first part gave a good influence on the rate of absorption.

The fiber density of the first part of the absorbent member of the tampon is preferably 0.5 g/cm³ or lower, more preferably 0.2 to 0.4 g/cm³. The fiber density of the second part is adequately 0.5 to 0.8 g/cm³. The overall average density of the absorbent member of the tampon is desired to be 0.7 g/cm³ or lower. An absorbent member of a tampon having an average density above that value is essentially so slow in absorption of a high-viscosity liquid such as menstrual blood that it may often leak along the side of the tampon. On the contrary, when the average fiber density of not only the first part but also the second part is as low as, for example, 0.2 g/cm³ or less, a high rate of absorption of blood can be secured without use of a fiber sheet-like material against which a liquid is ejected as in the present invention. However, such a tampon with a low average fiber density has a low capacity of absorption and, hence, is unsatisfactory as a tampon. As a result of some tests, it is preferred that a volume ratio of the first part to the entire absorbent member is 30% or larger, more preferably 30 to 70%, most preferably 40 to 70%. When a volume proportion of proratio of the first part is less than 30%, the initial rate of absorption of menstrual blood happens to be slow. On the other hand, when the volume proportion of the first part exceeds 70%, the capacity of absorption happens to be comparatively low.

The absorbent member of the tampon according to the present invention has a lower fiber density in the first part constituting the front portion than the fiber density in the second part constituting the rear portion, and a reduced amount of a lubricant sticking to the fiber. Therefore, the initial rate of absorption of a high-viscosity liquid such as menstrual blood is so high that the tampon can absorb menstrual blood without leakage thereof even when 3 to 5 g of menstrual blood is discharged at once. Furthermore, since the absorbent member of the tampon according to the present invention comprises a fiber sheet-like material compression-molded into the absorbent member, which is formed by ejecting a liquid against a fiber laminate, the proportion of a minute and/or short fibers contained therein is so low that the amount of the fibers falling off from the tampon at the time of service thereof is by far small as compared with those in the case of conventional absorbent members of tampons.

The absorbent member of the tampon mounted on a so-called applicator (inserting device) is, of course, included in the scope of this invention, too.

We claim:

1. An absorbent member having a front part and a rear part which comprises a first portion on the front part and a second portion on the rear part, said first portion having a smaller fiber density than the second portion wherein said density increases along the longitudinal direction of said member.

2. An absorbent member as claimed in claim 1, wherein said first portion has a fiber density of no greater than 0.5 g/cm$^3$ on the average and said member on the whole has a fiber density of no greater than 0.7 g/cm$^3$ on the average.

3. An absorbent member as claimed in claim 1, wherein said first portion occupies a volume of from 30 to 70 percent.

4. An absorbent member as claimed in claim 1, wherein the member is a tampon.

5. An absorbent member as claimed in claim 1, wherein said member comprises interlaced fibers.

6. An absorbent member having a front part and a rear part, which comprises a first portion on the front part and a second portion on the rear part, said first portion having a smaller fiber density than the second portion, said member having been produced by ejecting a liquid against a sheet of water-absorptive fibers in order to interlace the fibers with each other and molding said sheet under sufficient pressure to form the absorbent member.

7. An absorbent member as claimed in claim 6, wherein said first portion has a fiber density of no greater than 0.5 g/cm$^3$ on the average and said member on the whole has a fiber density of no greater than 0.7 g/cm$^3$ on the average.

8. An absorbent member as claimed in claim 6, wherein the first portion occupies a volume of from 30 to 70 percent.

* * * * *

UNITED STATES PATENT AND TRADEMARK OFFICE
CERTIFICATE OF CORRECTION

PATENT NO. : 4,714,466

DATED : December 22, 1987

INVENTOR(S) : Masatake Dohzono et al.

It is certified that error appears in the above-identified patent and that said Letters Patent is hereby corrected as shown below:

Column 10, delete Claim 6 and 8.

On the title page, "8 Claims" should read -- 5 Claims --.

Signed and Sealed this

Nineteenth Day of July, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,714,466

DATED : December 22, 1987

INVENTOR(S) : Masatake DOHZONO et al

It is certified that error appears in the above-identified patent and that said Letters Patent is hereby corrected as shown below:

Column 10, delete Claim 7.

Signed and Sealed this

Twenty-second Day of November, 1988

*Attest:*

DONALD J. QUIGG

*Attesting Officer*  *Commissioner of Patents and Trademarks*